United States Patent [19]

Agee et al.

[11] Patent Number: 5,306,284
[45] Date of Patent: Apr. 26, 1994

[54] SURGICAL INSTRUMENT

[75] Inventors: John M. Agee, 77 Scripps Dr., Sacramento, Calif. 95822; Francis King, Sacramento, Calif.; Kimberly A. Romanko, St. Paul, Minn.; Lawrence A. Flor, St. Paul, Minn.; Thomas A. Turgeon, St. Paul, Minn.; William A. Mittelstadt, St. Paul, Minn.

[73] Assignees: John Agee, Sacramento, Calif.; Minnesota Mining & Mfg. Co., St. Paul, Minn.

[21] Appl. No.: 838,532

[22] Filed: Feb. 19, 1992

[51] Int. Cl.$^5$ ............................................. A61B 17/32
[52] U.S. Cl. .................................................... 606/170
[58] Field of Search ............... 606/167, 170, 159; 128/3-6, 750-755; 604/117, 22

[56] References Cited

U.S. PATENT DOCUMENTS

| | | |
|---|---|---|
| Re. 321,158 | 5/1986 | Vukovic . |
| 344,984 | 7/1986 | Price . |
| 348,843 | 9/1986 | Hamilton . |
| 1,632,290 | 6/1927 | Heymer . |
| 3,900,022 | 8/1975 | Widran . |
| 4,137,920 | 2/1979 | Bonnet . |
| 4,200,111 | 4/1980 | Harris . |
| 4,201,199 | 5/1980 | Smith . |
| 4,201,213 | 5/1980 | Townsend . |
| 4,258,716 | 3/1981 | Sutherland . |
| 4,275,735 | 6/1981 | Chutter . |
| 4,423,727 | 1/1984 | Widran et al. . |
| 4,461,280 | 7/1984 | Baumgartner . |
| 4,474,174 | 10/1984 | Petruzzi . |
| 4,499,899 | 2/1985 | Lyons, III . |
| 4,522,206 | 6/1985 | Whipple . |
| 4,539,976 | 9/1985 | Sharpe . |
| 4,580,563 | 4/1986 | Gross . |
| 4,603,694 | 8/1986 | Wheeler . |
| 4,620,547 | 11/1986 | Boebel . |
| 4,633,860 | 1/1987 | Korth et al. . |
| 4,726,370 | 2/1988 | Karasawa . |
| 4,729,374 | 3/1988 | Alfranca . |
| 4,819,620 | 4/1989 | Okutsu . |
| 4,850,342 | 7/1989 | Hashiguchi et al. . |
| 4,962,770 | 10/1990 | Agee et al. . |
| 4,963,147 | 10/1990 | Agee et al. . |
| 5,089,000 | 2/1992 | Agee et al. . |

FOREIGN PATENT DOCUMENTS

| | | |
|---|---|---|
| 0212308 | of 1986 | European Pat. Off. . |
| 2903471 | 2/1979 | Fed. Rep. of Germany . |
| 2737014 | 3/1979 | Fed. Rep. of Germany . |
| 2748057 | 5/1979 | Fed. Rep. of Germany . |
| 3408243 | 9/1985 | Fed. Rep. of Germany . |
| 2151929 | 7/1985 | United Kingdom . |

OTHER PUBLICATIONS

Okutsu et al., "Universal Endoscope", Journal of the Japanese Orthopedic Association, vol. 61, No. 5 (1987).
Paine, Kenneth W. E., M.D. et al., "Carpal Tunnel Syndrome", J. Neurosurg., 59:1031-1036 (1983).
Ruggles Corporations, "Neurosurgical Instruments", Bulletin No. 795415, 5 pages.
Okutsu et al., "Universal Subcutaneous Endoscope", Journal of the Japances Anthroscopic Association, vol. 12, No. 1 (1987).

*Primary Examiner*—Peter A. Aschenbrenner
*Assistant Examiner*—Wm. Lewis
*Attorney, Agent, or Firm*—Dean P. Edmundson

[57] ABSTRACT

Surgical instruments are disclosed for manipulating selected tissue in a body cavity under visual inspection. The preferred instrument includes a probe in which a blade is positioned, wherein the probe includes a lateral aperture near its distal end. The blade can be extended outwardly from the probe along a path which is essentially perpendicular to the longitudinal axis of the probe. After the blade has been extended it can be used to effectively divide tissue. An optical system can be received in the probe for viewing through the lateral aperture in the probe.

63 Claims, 11 Drawing Sheets

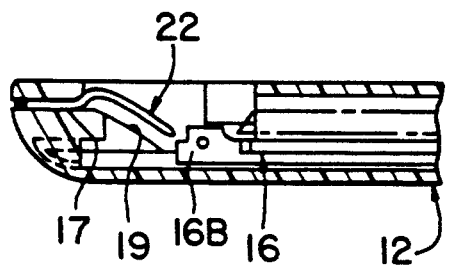
F I G. 3
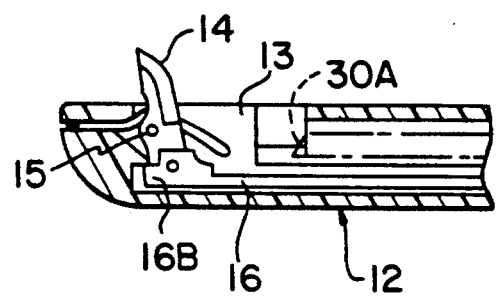
F I G. 4
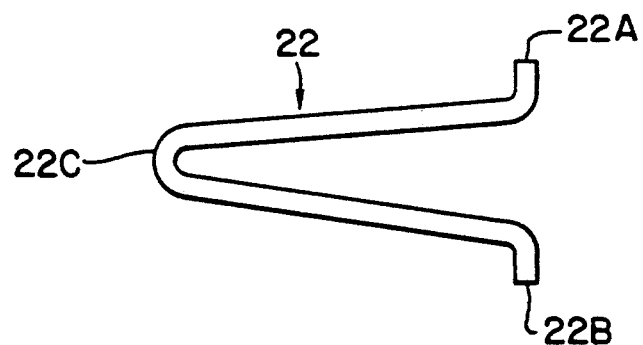
F I G. 5A
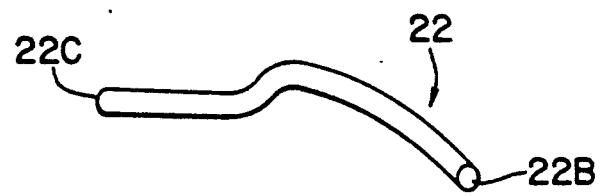
F I G. 5B

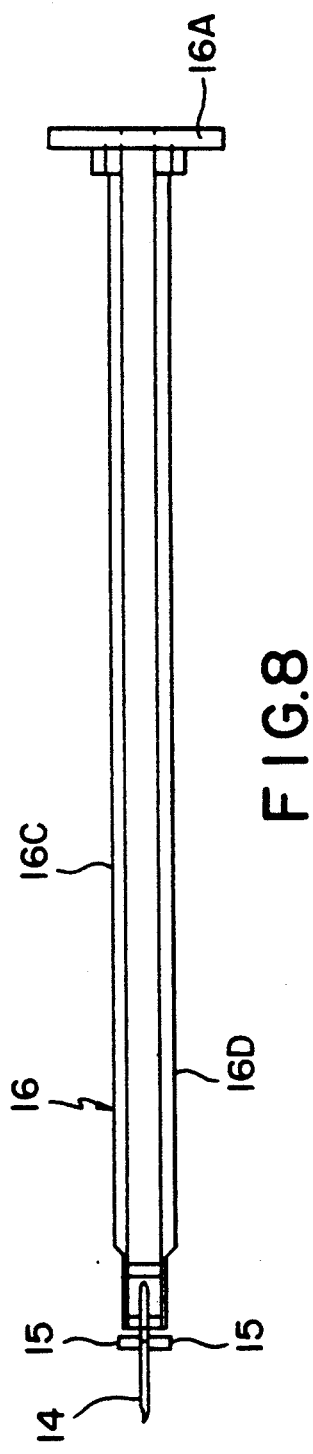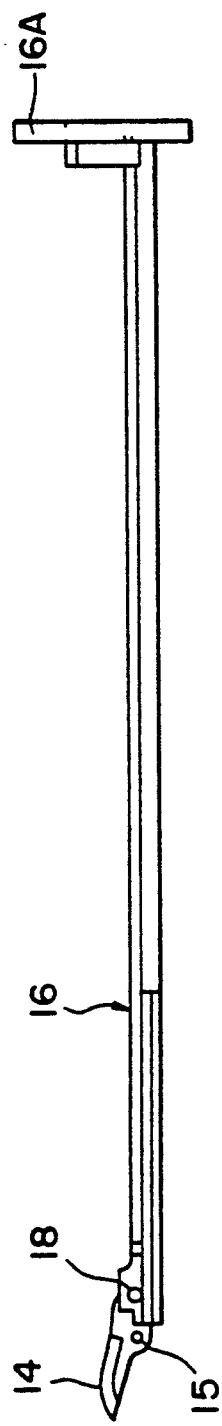

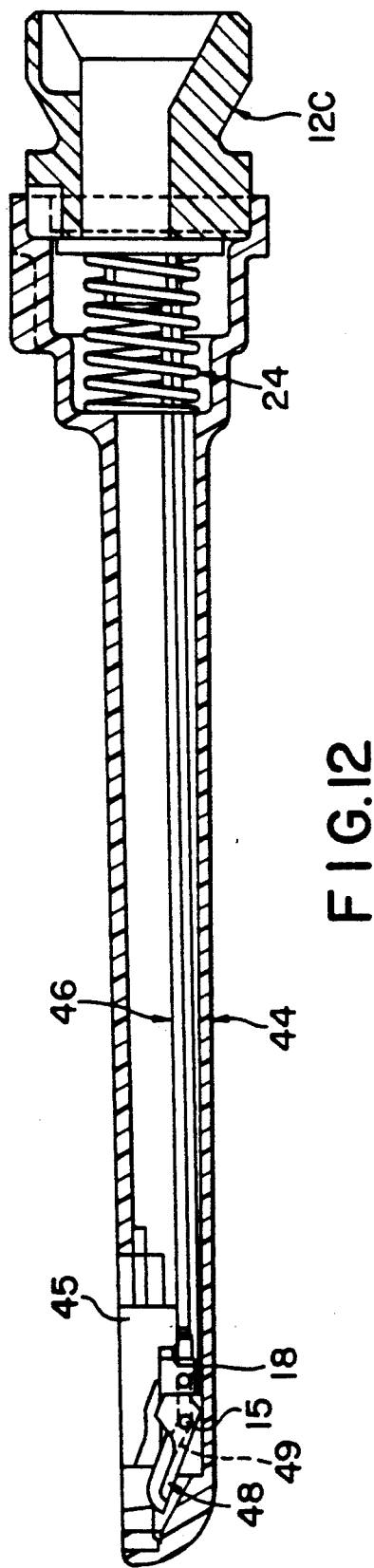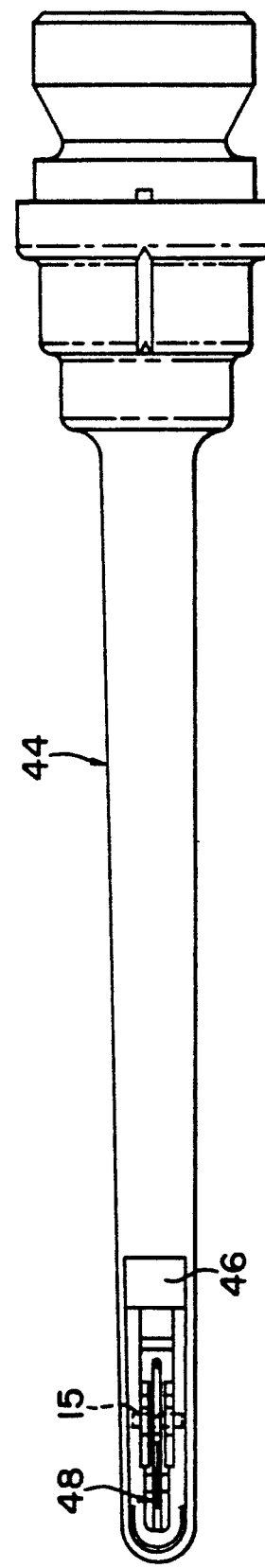

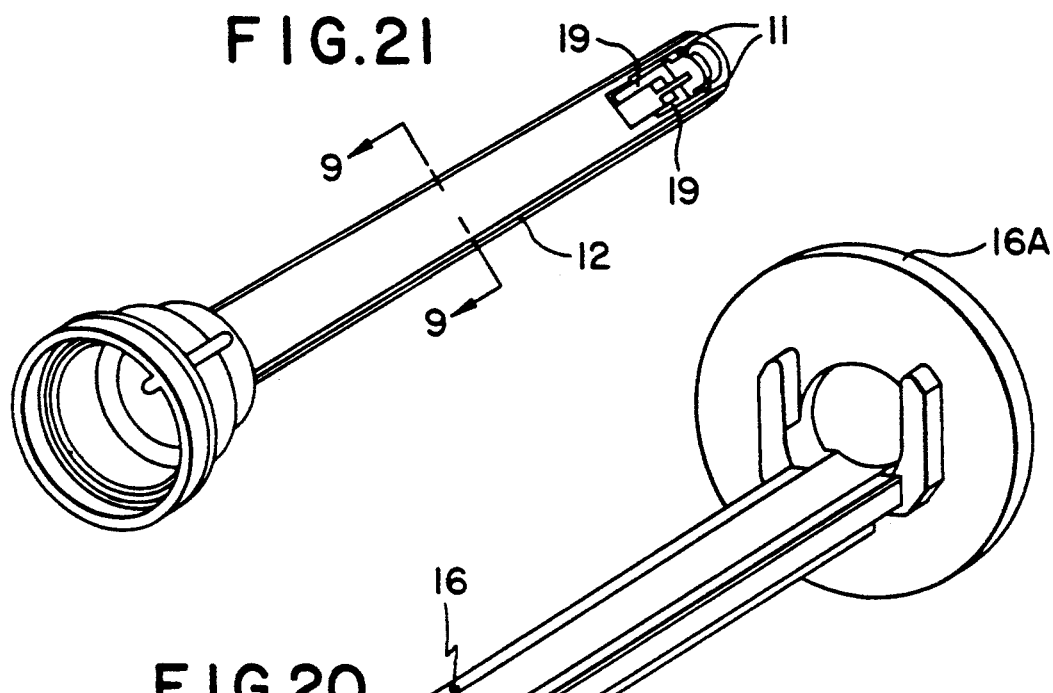
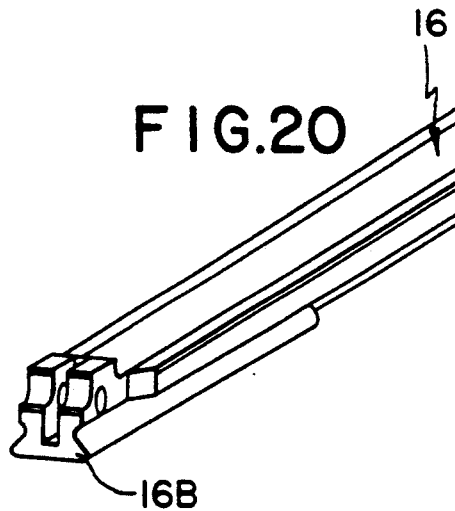

SURGICAL INSTRUMENT

FIELD OF THE INVENTION

This invention relates to surgical instruments. More particularly, this invention relates to surgical instruments for probing body cavities and manipulating tissue contained therein under continuous observation.

BACKGROUND OF THE INVENTION

U.S. Pat. Nos. 4,963,147; 4,962,770; and 5,089,000 incorporated herein by reference, describe a surgical instrument which is very useful in techniques for carpal tunnel release and is also useful in other surgical techniques. The instrument includes a probe in which a cutting blade and an optical system are disposed. After the probe has been inserted into a body cavity the cutting blade is extended through a lateral aperture in the probe to a position adjacent the selected tissue, while allowing the tissue manipulation to be observed.

In the surgical instrument just described the cutting blade extends through an axially fixed rotatable pivot pin. As an actuation shaft urges the cutting blade through the pivot pin, the distal end portion of the blade sweeps through an arc to reach a fully extended position. Initially the distal tip of the blade moves toward the distal end of the probe and then moves upwardly to its fully extended position. This forward movement of the tip of the blade can be undesirable because the tip can encounter tissue which is not intended to be cut. Also, the tip of the blade is not easily visible as it is being elevated.

SUMMARY OF THE PRESENT INVENTION

In accordance with the present invention there are provided improved surgical instruments for manipulating selected tissue in a body cavity under visual inspection. The instruments comprise blade means mounted within an elongated probe. Means are provided for extending a cutting blade outwardly from the probe in a nearly vertical path. The blade remains within the field-of-view of the optical system at all times. Also, because the tip of the blade does not move distally as it is elevated, it does not encounter unintended tissue. Accordingly, use of the surgical instruments of this invention can be very safe, enabling greater control over movement of the blade out of the probe.

In one embodiment of this invention there is provided an improved surgical instrument comprising:

(a) a probe having an upper surface, a generally closed distal end, and a lateral aperture in the upper surface and adjacent the closed distal end; wherein the distal end slopes away from the upper surface in a manner such that the distal end diverts displaceable tissue it contacts away from the region of the lateral aperture and the upper surface;

(b) means for accepting an optical system disposed at least partially within the probe, the system having a distal portion terminating adjacent the lateral aperture, thereby defining a viewing space between the distal portion of the optical system, and the distal end and the lateral aperture, the viewing space located within the field-of-view of the optical system;

(c) a working tool comprising blade means mounted within the probe and including a cutting blade capable of dividing selected tissue; wherein the cutting blade is capable of being extended from the viewing space; wherein the cutting blade includes a distal end portion;

(d) means for extending the cutting blade outwardly from the viewing space in a manner such that the distal end portion of the cutting blade follows a path which is essentially perpendicular to the longitudinal axis of the probe;

(e) a grip handle rotatably connected to the probe; and (f) adjustment means for adjusting the rotational orientation between the lateral aperture of the probe and the grip handle; wherein the adjustment means is adapted to temporarily fix the rotational orientation.

Other embodiments of surgical instruments are also provided in which the blade is elevated from the probe in a manner such that the tip of the blade does not move distally relative to the probe. Various mechanical embodiments are described which control the desired path of the blade as it is elevated. Marker means can also be included in the instrument to indicate the point-of-entry of the blade into tissue. This feature is another significant improvement over prior devices because it enables very precise placement of the blade relative to tissue to be divided.

Other advantages of the surgical instruments of this invention will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which:

FIG. 3 is a side elevational cut-away view of the distal tip of the probe of FIG. 1 (with blade removed);

FIG. 4 is a side elevational cut-away view of the probe of FIG. 1 with the cutting blade extended;

FIGS. 5A and 5B are top and side views of a clip member which is useful in the probe of FIG. 1;

FIG. 7 is a side elevational view of the actuator arm and cutting blade useful in the probe of FIG. 1;

FIG. 8 is a top view of the actuator arm and cutting blade of FIG. 7;

FIG. 12 is a side elevational cut-away view of another embodiment of surgical probe of the invention;

FIG. 13 is a top view of the probe of FIG. 12;

FIG. 20 is a perspective view of a preferred type of actuator arm useful in probes of this invention;

FIG. 21 is a perspective view of the housing or sheath of the probe shown in FIG. 1.

DETAILED DESCRIPTION OF THE INVENTION

The present invention provides improvements to surgical instruments of the type comprising an elongated tubular housing or sheath, a working tool (e.g., cutting blade) within the housing, and means for accepting an optical system. The surgical instruments of this type are useful in manipulating selected tissue in body cavities under continuous visual observation. For example, surgical instruments as described herein are especially useful in surgical procedures for dividing the transverse carpal ligament (flexor retinaculum) in order to decompress the median nerve in the carpal tunnel. Of course, the surgical instruments of this invention are also useful in a variety of other surgical procedures for manipulating tissue within a body cavity.

Figure 1:
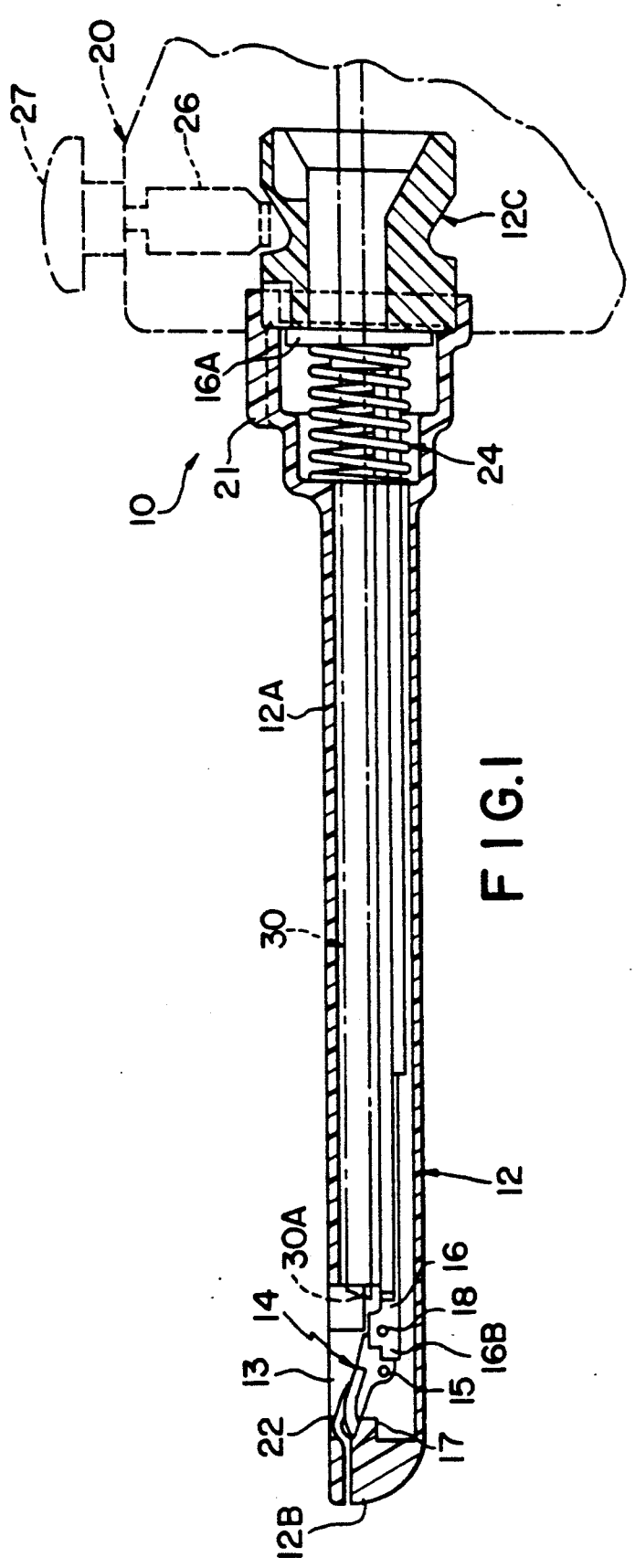
FIG. 1 is a side elevational cut-away view of one embodiment of surgical probe of this invention.
Figure 2:
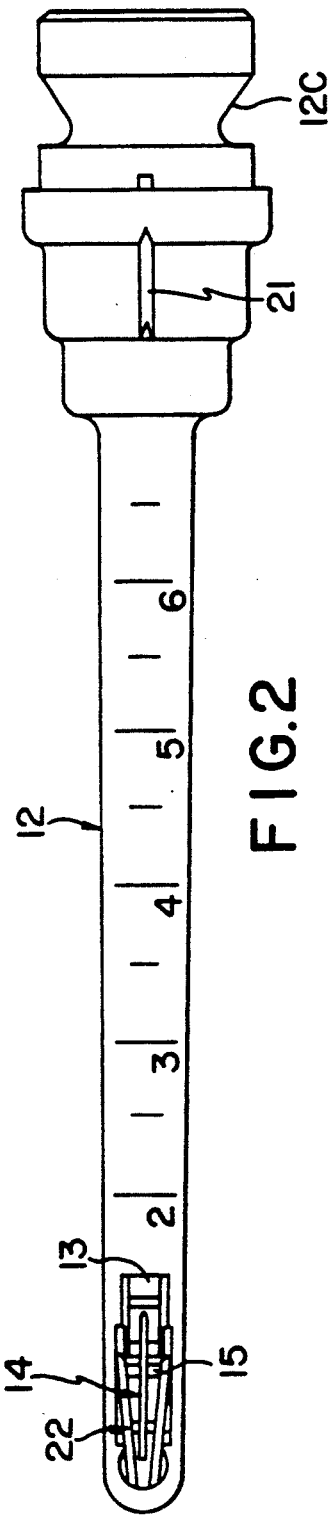
FIG. 2 is a top view of the surgical probe of FIG. 1.

In FIG. 1 there is illustrated in a side elevational cut-away view of one embodiment of surgical instrument 10 of the invention comprising an elongated probe 12 operably connected or attached to a holder 20. The holder 20 is more completely shown in FIG. 10. FIG. 2 is a top view of the probe.

The probe 12 includes an upper surface 12A, a generally closed distal end 12B, and a lateral aperture 13 in the upper surface adjacent the distal end of the probe. The upper surface of the probe is preferably flat (or slightly concave) in areas adjacent the lateral aperture. As illustrated, the distal end of the probe slopes downwardly away from the upper surface in a manner such that the distal end diverts displaceable tissue it contacts away from the region of the lateral aperture and the upper surface. The distal end may be slightly curved, as shown, or it may be inclined as a generally flat surface which forms an acute angle with the upper surface of the probe.

The housing or sheath of the probe is tubular and enables a conventional optical viewing scope 30 to be slidingly received in the probe through an opening at the proximal end of the probe. The scope 30 includes a distal end 30A which terminates adjacent the lateral aperture 13 to define a viewing space between the distal portion of the scope, and the distal end of the probe and the lateral aperture. The viewing space is located within the field-of-view of the optical system.

Near the proximal end of probe 12 there is a raised longitudinal rib 21 which is in alignment with the position of the blade 14 in the probe. The rib 21 is a useful indicator to signify the angular position of the blade after the probe has been inserted into a body cavity. The scale on the upper surface of the probe is also useful for indicating the length of probe already inserted into a body cavity.

Figure 11A:
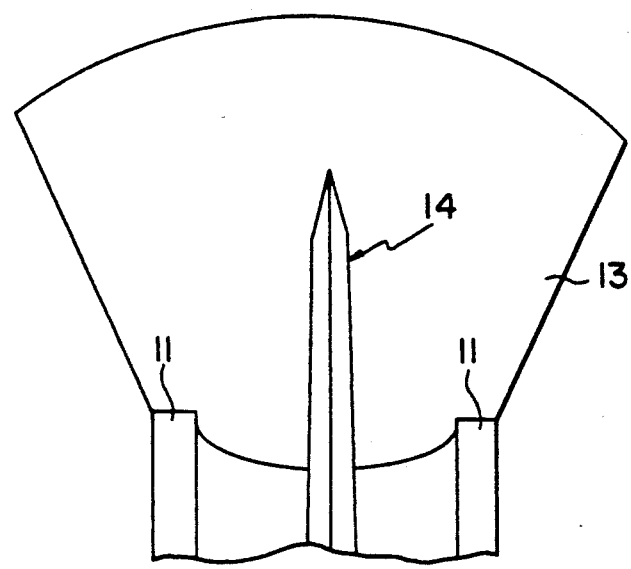
FIG. 11A is an enlarged view showing the blade elevated from the probe.
Figure 11:
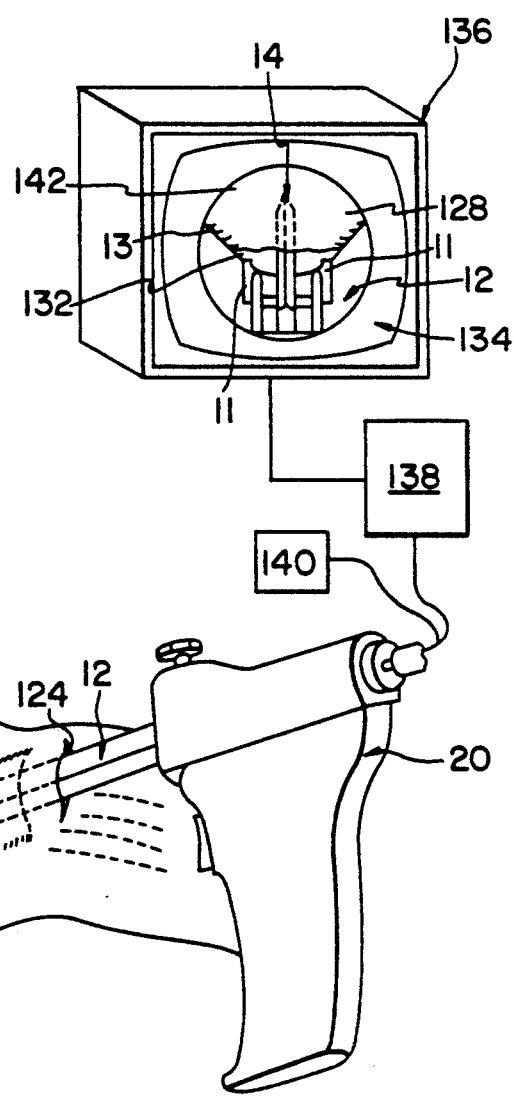
FIG. 11 is a diagrammatic view showing use of a surgical instrument of this invention operably connected to an optical viewing system (including a video monitor)

Blade means comprising a cutting blade 14 is carried within the probe near the distal end. The blade is movable between a retracted position (shown in FIGS. 1 and 2) and an elevated or extended position (shown in FIGS. 4 and 6) where it is capable of dividing selected tissue. When the blade is in its retracted position it does not contact body tissue. Thus, the distal end of the probe can easily and safely be inserted into a cavity in the body when the blade is in retracted position. Using the optical system contained at least partially within the probe, the user can manipulate and position the probe precisely where desired before extending the cutting blade. For example, the optical system can be operably connected to a conventional video monitor, as illustrated in FIG. 11.

The blade 14 is moved between its retracted and elevated positions by means of actuator arm or shaft 16 which is slidably movable within the probe. The proximal end 16A of the actuator shaft 16 includes a large plate or ring against which longitudinal force may be exerted to move the shaft toward the distal end of the probe (to elevate the blade) or toward the proximal end of the probe (to retract the blade). FIGS. 7 and 8 show the actuator shaft 16 in side view and top view, respectively. FIG. 20 is a perspective view of actuator 16 (with the blade 14 removed).

The force which is exerted on the plate 16A to move the shaft toward the distal end of the probe is provided by end 41 of shuttle 40 of the probe holder 20 (shown in FIG. 10), upon compression of trigger 34. The force which is exerted on the opposite face of plate 16A to cause the actuator shaft 16 to move away from the distal end is provided by spring 24 with the probe. The spring urges the actuator shaft away from the distal end of the probe so that the blade is in a normally retracted position.

Figure 22:
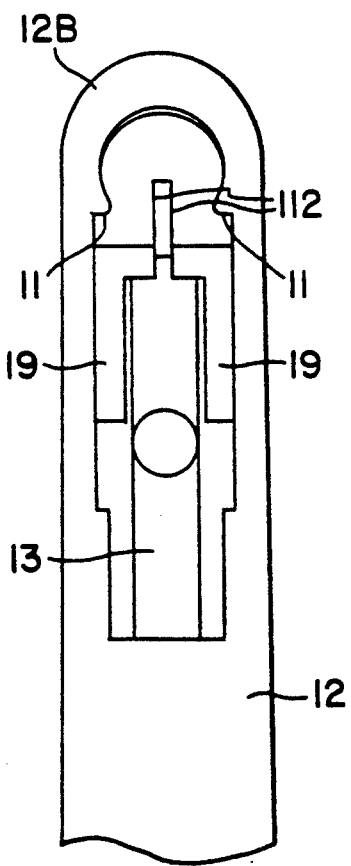
FIG. 22 is a top plan view of the distal end of the housing shown in FIG. 21.

As shown in the drawings, preferably one end of the cutting blade 14 is pivotally connected to the distal end of the actuator shaft by means of pin 18. It is also preferred for the blade to include transversely extending guide pins or cam rods 15 between the opposite ends of the blade. As shown in FIGS. 3, 21, and 22 the distal end of the probe includes cam means or ramp means 19 which is sloped upwardly toward the distal end of the probe adjacent the cutting blade. Preferably there are two such ramps, one adjacent each side of the cutting blade and positioned such that the guide pin 15 extending outwardly from each side of the blade is caused to slide upwardly along the ramp as the actuator shaft 16 is moved toward the distal end of the probe.

In this manner, the distal end of the cutting blade is caused to move from its retracted position to its extended position along a nearly vertical line. The vertical or extended position of the blade is shown in FIG. 4.

This feature of the tip of the cutting blade moving upwardly along a nearly vertical line is extremely significant because it enables the user of the instrument to accurately position the probe with respect to tissue to be divided such that the blade can be elevated to initiate cutting precisely where the user of the instrument desires.

Another significant feature which is illustrated in the drawings is the provision of marker means for indicating the point of entry of the blade into tissue. In the embodiment shown herein, the marker means comprises vertical wall sections or columns 11 near the distal end of the probe 12. Preferably there are two such markers (one on either side of the blade) which are located in line with the vertical path which the tip of the blade 14 follows when the blade is elevated. The provision of these markers is very helpful to the surgeon operating the instrument because the surgeon is then able to position the distal end of the probe at the desired location for blade entry before the blade is elevated. The markers are easily visible in the image shown on the video monitor (see FIGS. 11 and 11A). This helps prevent cutting of tissue at undesired locations when the blade is elevated.

When the actuator shaft 16 is moved away from the distal end of the probe so as to retract the cutting blade 14, clip member 22 secured in the probe provides an upper track surface for rod members 15 on the blade. The provision of these upper track surfaces for the rod members 15 assures that the blade fully retracts into the probe 12. In other words, the track surfaces provided by clip 22 cause rod members 15 on blade 14 to follow a defined downward path, thereby assuring that blade 14 moves to a downward or retracted position. Each rod member 15 on blade 14 is constrained in the cam track defined between ramp member 19 (on the lower side) and clip member 22 (on the upper side). This track controls both the upward movement of the blade to its extended position and also the downward movement of the blade to its retracted position.

Figure 6:
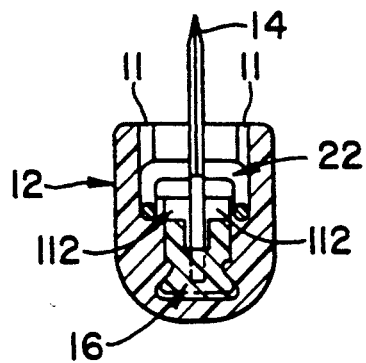
FIG. 6 is a cross-sectional view of the distal end of the probe of FIG. 1 with the cutting blade elevated.

Another important feature of the probe of this invention is illustrated in the drawings. This feature involves the provision of lateral support to the blade when it is in its elevated position. Lateral support is provided by opposing wall sections 112 in the distal end of the probe adjacent the blade. These supports are best shown in FIGS. 6, 21 and 22. The gap or slot between wall sections 112 receives the blade as it is elevated, and the wall sections provide lateral support to the blade so as to prevent wobble or lateral movement of the blade during use.

Another important feature of the probe illustrated in FIGS. 1 through 4 involves the distal end of the actuator shaft 16 which includes a forwardly projecting foot portion 16B which is captured under ledge portion 17 of the distal end of the probe when the actuator shaft is moved to the position shown in FIG. 4 (i.e., to the position where the blade 14 is completely elevated). Because the distal end of the actuator shaft is captured under ledge 17 when the blade is fully extended, force exerted against blade 14 cannot cause the distal end of the actuator shaft to deflect or to be forced upwardly. Also, as shown in FIGS. 6 and 20, the base of the actuator shaft near its distal end is flared outwardly (like a dovetail) so that it has a shape complementary to the flared portion of the cavity in the distal end of the probe. Consequently, when the blade 14 is in its fully extended position for cutting purposes, the blade cannot be caused to deflect distally relative to the probe during cutting.

FIGS. 5A and 5B illustrate the clip member 22 which has been described above. Preferably the clip member includes two elongated rail portions (each rail being adapted to define an upper track surface for rod member 15 extending outwardly from blade 14. The free ends 22A and 22B of the clip are secured in the opposite side walls, respectively, of the probe. The forward end 22C of the clip is received in an appropriate slot at the distal end of the probe 12 so that the clip member is very securely retained in the probe in the desired position.

As illustrated in FIG. 1, the proximal end of probe 12 is connected to holder 20. For example, the proximal end of probe 12 may include an annular recess 12C into which a movable bolt 26 may be positioned to capture or retain the probe in the holder 20. The position of bolt 26 may be vertically adjusted by means of knob 27. In other words, by loosening knob 27 to raise bolt 26, the probe may be removed from the holder 20. Alternatively, by tightening knob 27, bolt 26 is urged tightly against probe 12 to secure it in a fixed position. With slight loosening of knob 27, the probe 12 may be rotationally adjusted relative to the holder 20.

Figure 9:
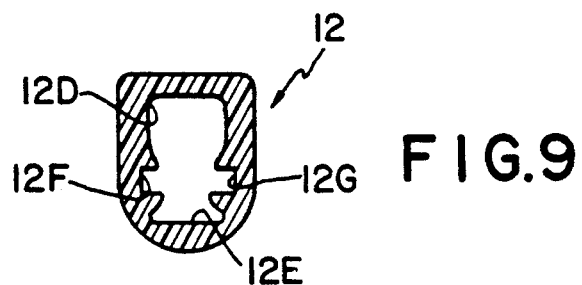
FIG. 9 is a cross-sectional view of the housing or sheath of the probe shown in FIG. 1.

FIG. 9 illustrates a preferred cross-sectional view of tubular probe 12 taken along line 9—9 in FIG. 21. The elongated cavity defined within the probe includes an upper section or portion 12D for slidably receiving the optical scope 30. The actuator shaft 16 is slidably received in the lower portion 12E of the cavity. Preferably the actuator shaft includes laterally extending ribs 16C and 16D which are received and retained in grooves 12F and 12G in the side walls of the probe 12. In this manner, the actuator shaft is prevented from twisting or bending relative to probe 12 during operation.

The probe housing, as illustrated, preferably has a D-shaped cross-section. The top surface of the probe is preferably flat (or slightly concave). Opposite side edges are parallel to each other, and the lower surface is curved (i.e., convex).

Figure 10:
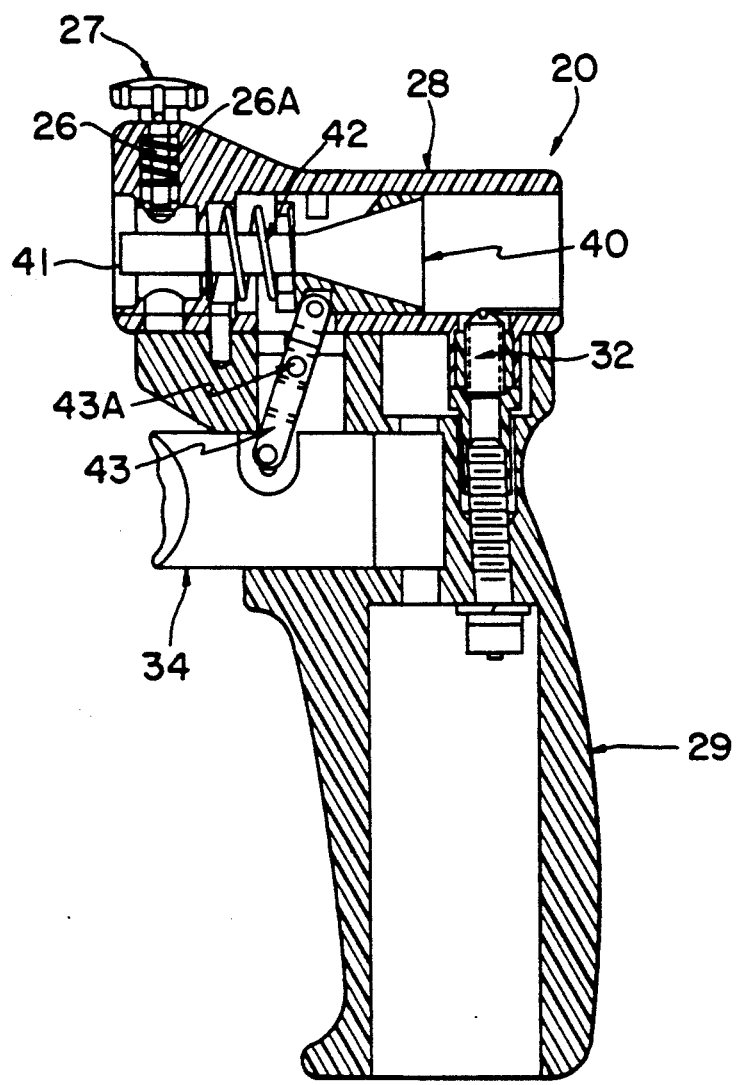
FIG. 10 is a side elevational cut-away view of a preferred instrument or holder in which the surgical probes of this invention may be used.

FIG. 10 is a side elevational cut-away view illustrating a preferred embodiment of holder 20 for the surgical probes. The holder comprises a grip handle portion 29 and an upper body portion 28. The proximal end of a probe 12 is slidably received in an opening at the forward end of body 28, and locking bolt 26 can be urged downwardly by rotating knob 27 to capture the probe therein. Spring 26A urges the bolt upwardly when the knob is loosened. Shuttle 40 is located within body 28 and includes a forward end 41 which rests against plate 16A on the actuator shaft in the probe when the probe is inserted into the holder. The shuttle 40 is operably connected to trigger 34 by means of pivotally mounted arm 43 (which can pivot about pin 43A). When the trigger is pulled toward the handle, the arm 43 causes the shuttle to move forwardly, whereby end 41 of the shuttle urges the actuator 16 toward the distal end of the probe to elevate the blade. The further the trigger is pulled, the greater the extent of elevation of the blade. Spring 42 urges the shuttle 40 rearwardly to its normal resting position.

A conventional elongated optical scope can be slidingly received through body 28 and shuttle 40. A spring-loaded ball assembly 32 is adapted to retain the optical scope in the holder during use.

FIG. 11 illustrates use of a surgical instrument of this invention for the purpose of performing carpal tunnel release by dividing the transverse carpal ligament (flexor retinaculum) 128 in order to decompress the median nerve in the carpal tunnel. The preferred use of the surgical instrument in performing carpal tunnel release is accomplished by forming a short transverse incision 124 located proximal to the carpal tunnel and the wrist flexion crease. After longitudinal spreading dissection, to avoid injury to the sensory nerves, the incision 124 is continued through the deep fascia of the forearm, the distal extension of which leads to the flexor retinaculum. After an incision through the finger flexor synovium, extension of the wrist will then expose the proximal opening of the carpal tunnel, thereby forming a passage to the carpal tunnel.

After adjusting the rotational orientation of the probe 12 relative to the holder 20 to accommodate a comfortable working position for the surgeon, the probe 12 is inserted through incision 124 and desirably through the length of the carpal tunnel to the distal edge 132 of the flexor retinaculum 128.

By employing the optical system, and through manipulation of the patient's extremities, the anatomy within the carpal tunnel can be clearly visualized on the display 134 of video monitor 136 and the structures defined, and the distal edge 132 can be located. The image conveyed to monitor 136 by video camera 138 can be enhanced by light source 140.

The distal end of probe 12 will desirably have gently displaced the tendons, bursa and median nerve found within the carpal tunnel to facilitate insertion of the probe. Then the lateral aperture of the probe will be positioned adjacent the medial surface 142 of the flexor retinaculum 128 and, desirably, the configuration of the probe upper surface (which is preferably a flat surface) will exclude the displaced tissues from the region surrounding the lateral aperture. The markers 11, which indicate the point on the probe where the blade elevates, are clearly visible on the display 134 to facilitate proper placement of the probe relative to the distal edge 132 of the flexor retinaculum 128.

Preferably the lateral aperture 13 in the upper surface of the probe extends distally past the cutting blade so that it is possible to view beyond the markers 11 (for the purpose of assuring that no undesirable tissue is located extremely close to the point where the blade elevates). FIG. 11A shows that the distal end of the aperture 13 is visible on the monitor past the location of blade 14.

At the appropriate location, blade 14 will be extended to enable the blade to contact the distal edge 132 of the flexor retinaculum 128, while the surgeon views the tissue to be divided via the display 134. The blade point will desirably be extended to a position sufficient to completely release the ligament.

While viewing (through the lateral aperture) the intended path of the extended cutting blade, the probe 12 is then withdrawn, thereby dividing the flexor retinaculum 128 and releasing the carpal tunnel. In the event of incomplete division, the steps above can be repeated with greater elevation of the cutting blade.

FIGS. 12 and 13 illustrate another embodiment of surgical probe of the invention. In this embodiment the housing or sheath of the probe is essentially the same as that described above with respect to the embodiment of FIG. 1. It is capable of being connected to the holder 20 in the same manner.

In the embodiment of FIGS. 12 and 13 a cutting blade 48 is pivotally attached at its proximal end to actuator shaft 46 in probe 44 by means of pin 18. Blade 48 includes a pin or rod 15 which extends outwardly transversely from each side edge of the blade. Rods 15 on opposite sides of blade 48 are received in grooves 49 in the opposite side walls of the probe body 44. The grooves are inclined upwardly toward the distal end of the probe. Consequently, as the actuator shaft 46 is moved toward the distal end of the probe, the rods 15 carried by blade 48 are caused to travel upwardly along the grooves 49 so as to elevate the distal end of the blade 48 out through aperture 45 in a nearly vertical manner. When the actuator shaft is moved away from the distal end of the probe, the rods 15 traveling in grooves 49 cause the cutting blade to move from its extended position to its retracted position.

Figure 14:
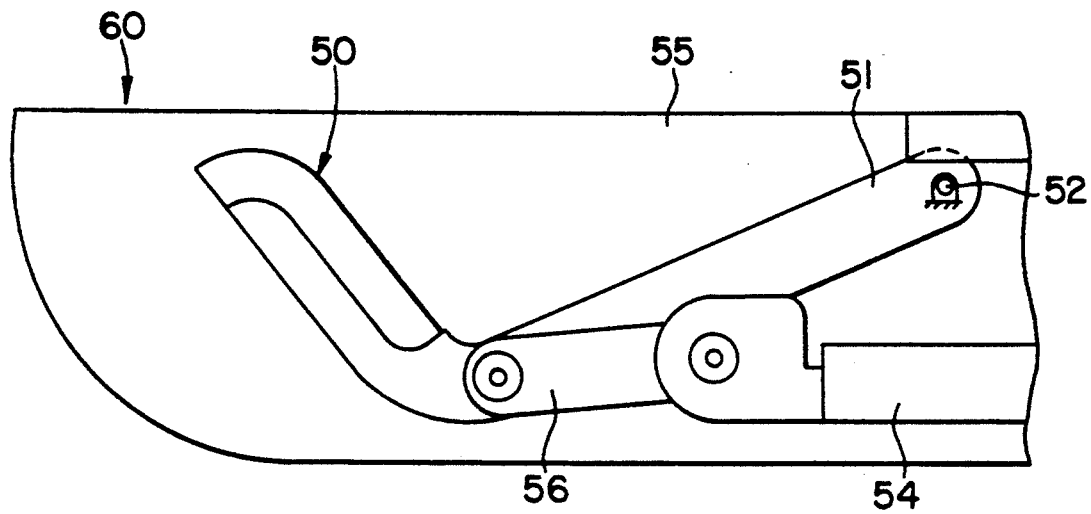
FIG. 14 is a side elevational cut-away view of the distal end of a surgical probe showing another blade elevating means.
Figure 15:
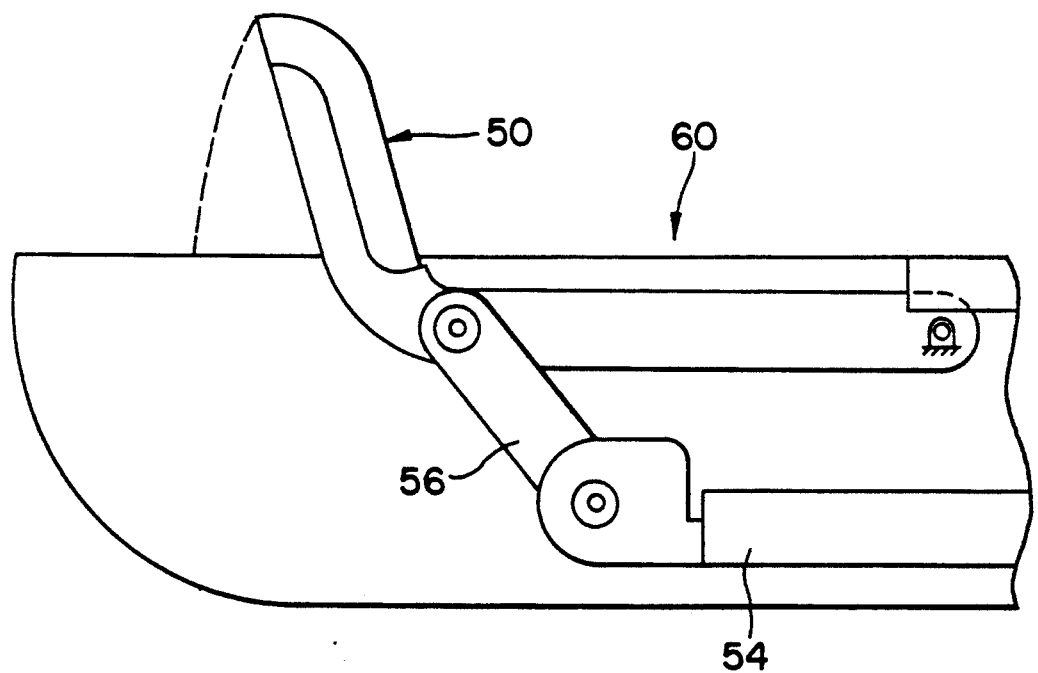
FIG. 15 is a side elevational cut-away view of the probe of FIG. 14 showing the blade after it has been elevated.

FIGS. 14 and 15 are side elevational views illustrating another manner in which the cutting blade can be elevated above the upper surface of a probe by means of movement of an actuator shaft. The probe includes a lateral aperture 55 in its upper surface.

Thus, in FIG. 14 the blade 50 includes a leg member 51 which is pivotally secured to the body of the probe 60 by means of pin 52. Actuator shaft 54 is connected to cutting blade 50 by means of a pivoting link 56. The link 56 is pivotally mounted at one end to the distal end of shaft 54 and is pivotally mounted at its opposite end to blade 50. As illustrated in FIG. 15, when the actuator shaft 54 is moved toward the distal end of the probe 60 the blade 50 is caused to be elevated above the upper surface of the probe. The path of the distal end of the cutting blade is shown in dotted line. In this embodiment the distal end of the cutting blade moves through a slightly arced path which is acceptable because the cutting blade is always moving away from the distal end of the probe.

Figure 16:
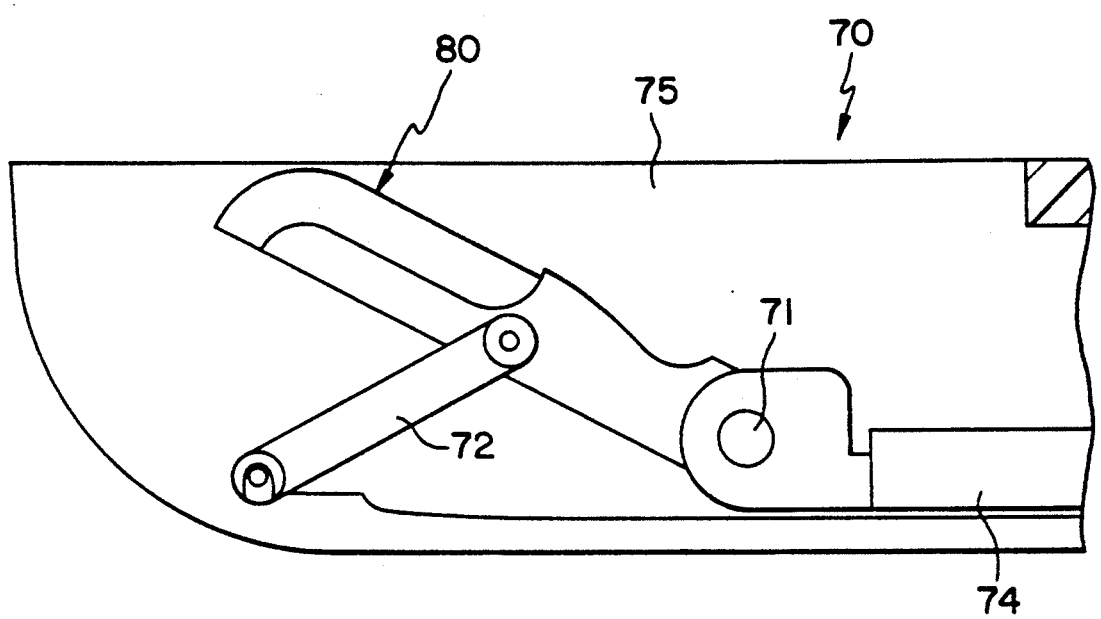
FIG. 16 is a side elevational cut-away view of the distal end of a surgical probe showing another blade elevating means.
Figure 17:
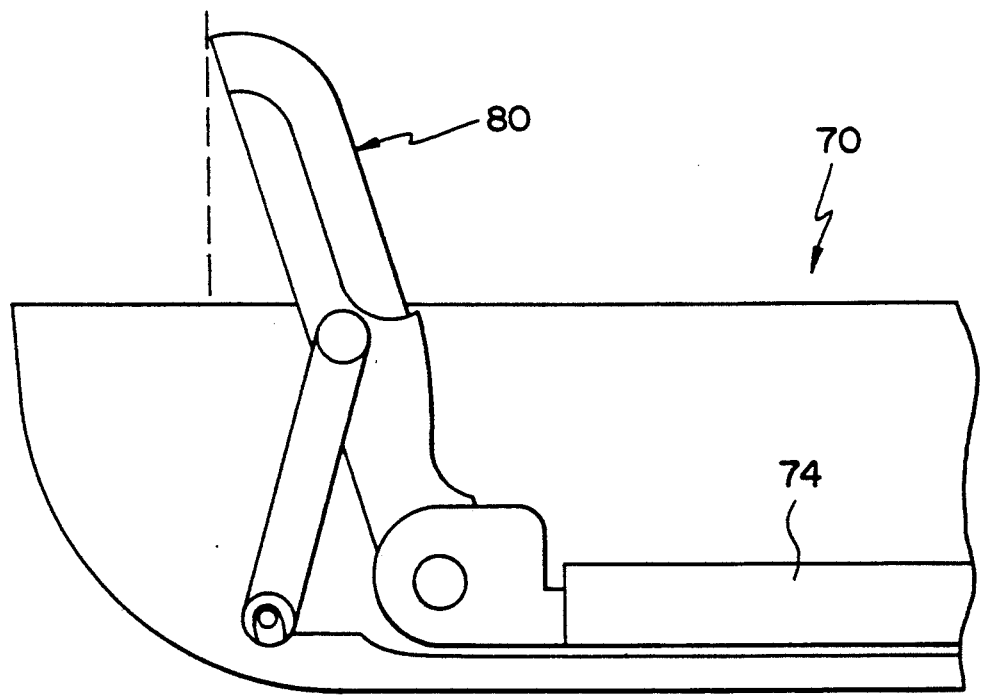
FIG. 17 is a side elevational cut-away view of the probe of FIG. 16 showing the blade after it has been elevated.

FIGS. 16 and 17 are side elevational views illustrating another manner in which a cutting blade can be elevated above the upper surface of a probe by means of movement of an actuator shaft. In FIG. 16 there is shown a probe 70 in which a cutting blade 80 is pivotally mounted at one end to the distal end of an actuator shaft 74 by means of pin 71. A link 72 is pivotally mounted at one of its ends to blade 80 and is pivotally mounted to the body of the probe at its opposite end. The probe includes a lateral aperture 75. As illustrated in FIG. 17, when the actuator shaft 74 is moved toward the distal end of the probe the distal end portion of the blade 80 is caused to be elevated along a vertical line above the upper surface of the probe. This is a very desirable blade elevation path.

Figure 18:
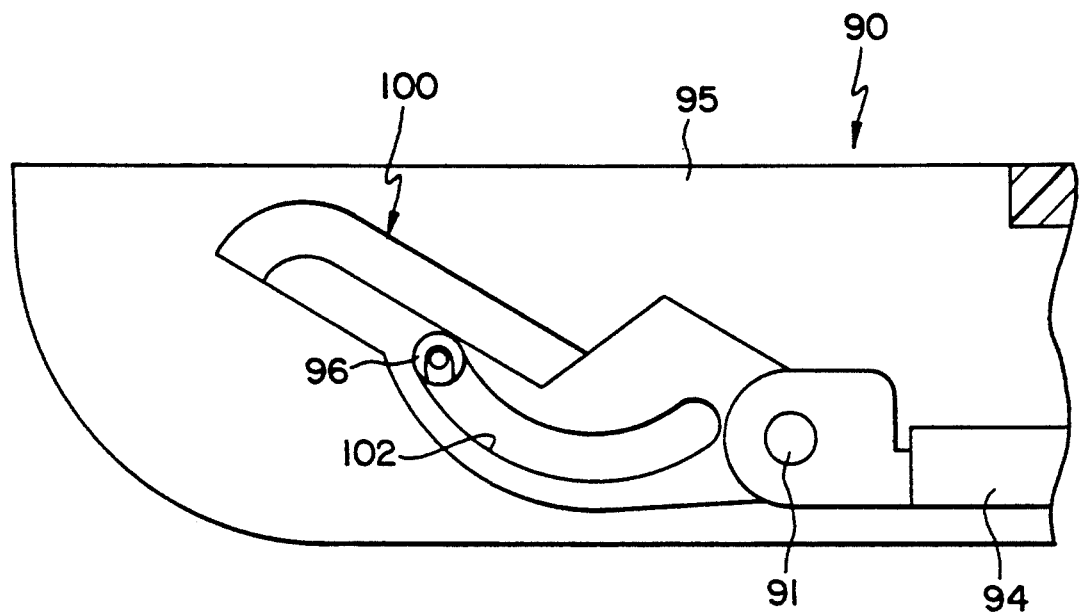
FIG. 18 is a side elevational cut-away view of the distal end of a surgical probe showing another blade elevating means.
Figure 19:
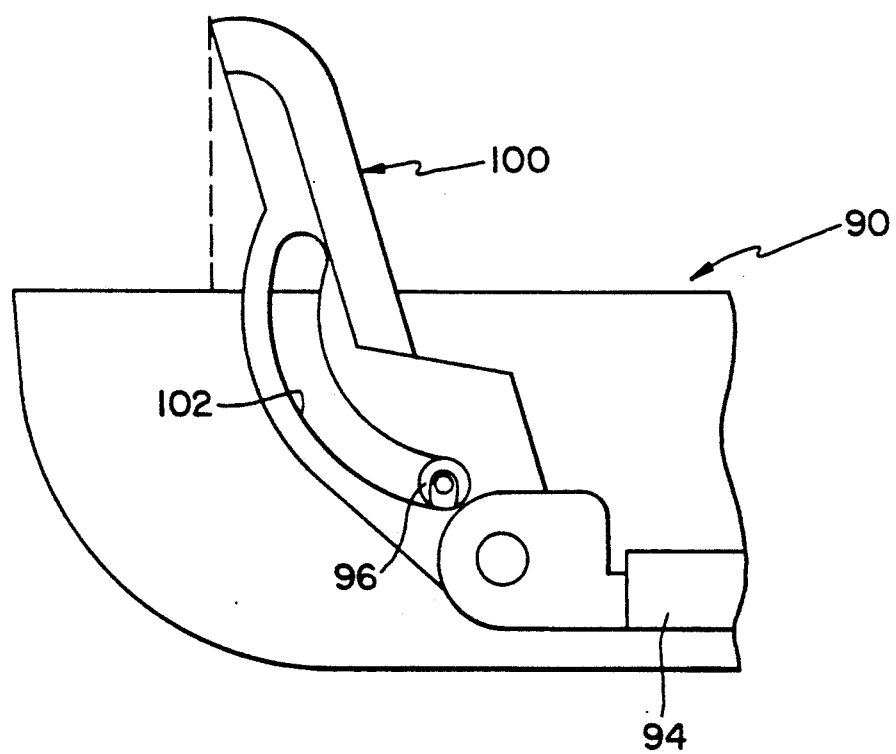
FIG. 19 is a side elevational cut-away view of the probe of FIG. 18 showing the blade after it has been elevated.

FIGS. 18 and 19 are side elevational views illustrating another manner in which a cutting blade can be elevated above the upper surface of a probe by means of movement of an actuator shaft. In FIG. 18 there is shown a probe 90 (having lateral aperture 95) in which a cutting blade 100 is pivotally mounted at one end to the distal end of an actuator shaft 94 by means of pin 91. The cutting blade includes a curved slotted aperture 102, as illustrated. Positioned in the slotted aperture is a pivot pin 96 which is secured to the body of the probe. As illustrated in FIG. 19, when the actuator shaft 94 is moved toward to the distal end of the probe, the cutting blade is caused to be elevated above the upper surface of the probe. The curved slotted aperture 102 moving with respect to the fixed pivot point 96 causes the blade to be elevated in a manner such that the distal end portion of the blade 100 moves upwardly along a desirable vertical line.

In the probes of this invention, as illustrated, the lateral aperture is located near the distal end of the probe in the upper surface thereof. Of course, the exact location of the lateral aperture may vary as desired. Although normally the blade is intended to be elevated out of the probe through the lateral aperture, it is possible of course for the blade to be elevated out of a separate aperture in the probe. Preferably the distal end of the lateral aperture extends beyond the location of the blade, as illustrated in the drawings herein.

The probe housing and actuator arm are preferably made of durable plastic so that the probe is economically disposable. The holder for the probe may be made of metal, durable plastic, or composite materials.

Other variants are possible without departing from scope of the present invention. It is understood that within the scope of the appended claims, the invention may be practiced otherwise than as is specifically described herein.

What is claimed is:

1. A surgical instrument for manipulating selected tissue in a body cavity under visual inspection, comprising:
   (a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface;
   (b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;
   (c) a working tool comprising blade means mounted within the probe and including a cutting blade capable of dividing selected tissue; wherein said cutting blade is capable of being extended from the viewing space; wherein said cutting blade includes a distal end portion;
   (d) means for extending said cutting blade outwardly from the viewing space in a manner such that said distal end portion of said cutting blade follows a path which is essentially perpendicular to the longitudinal axis of said probe;
   (e) a grip handle rotatably connected to said probe; and
   (f) adjustment means for adjusting the rotational orientation between said lateral aperture of said probe and said grip handle; wherein said adjustment means is adapted to temporarily fix said rotational orientation.

2. An instrument as recited in claim 1, wherein the grip handle comprises actuator means for extending said blade means out of the probe.

3. An instrument as recited in claim 2, wherein the instrument further comprises means for automatically retracting said blade means upon release of the actuating means.

4. An instrument as recited in claim 1, wherein the distal end of said probe is configured generally as an inclined plane which forms an acute angle with the upper surface of the probe.

5. An instrument as recited in claim 1, wherein means for accepting an optical system accommodates a conventional examination telescope.

6. An instrument as recited in claim 1, wherein the means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of said cutting blade.

7. An instrument as recited in claim 6, wherein said actuation shaft is adapted to respond to actuating movement by an operator of the instrument; and wherein each additional increment of longitudinal displacement of the actuation shaft produces a correspondingly greater increment in the extension of said cutting blade.

8. An instrument in accordance with claim 6, wherein said cutting blade includes a proximal end which is pivotally connected to said actuation shaft; and further comprising elevating means for elevating said distal end portion of said cutting blade in response to longitudinal displacement of said actuation shaft.

9. An instrument as recited in claim 6, wherein the working tool is cooperatively engaged with an axially fixed pivot in the distal en of the probe so that longitudinal displacement of the actuation shaft produces an angular displacement of the working tool as the actuation shaft approaches the pivot, thereby outwardly extending said cutting blade.

10. An instrument in accordance with claim 1, further comprising marker means at said distal end of said probe for indicating the position of said distal end portion of said cutting blade relative to the longitudinal axis of said probe.

11. An instrument in accordance with claim 1, wherein said probe is detachably connected to said grip handle and is disposable.

12. An instrument in accordance with claim 1, wherein the upper surface adjacent to the lateral aperture is configured generally as a flat or concave surface.

13. An instrument in accordance with claim 1, wherein said probe includes a flat upper surface, parallel sides, and a convex lower surface.

14. A surgical instrument in accordance with claim 1, wherein said distal end of said probe further comprises blade support means for providing lateral support to said blade when said blade is elevated relative to said probe.

15. A surgical instrument in accordance with claim 14, wherein said blade support means is integral with said distal end of said probe.

16. A surgical instrument in accordance with claim 15, wherein said blade support means comprises wall members adjacent said blade.

17. A surgical instrument in accordance with claim 16, wherein said wall members include opposing wall faces defining a gap therebetween, and wherein said blade is received in said gap.

18. A surgical instrument for dividing the flexor retinaculum under visual inspection during carpal tunnel release, while minimizing the risk of injury to surrounding tissue, comprising:
   (a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface; wherein said upper surface of said probe adjacent to said lateral aperture is configured generally as a flat or concave surface;
   (b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;

(c) a cutting blade mounted within the viewing space and capable of being extended from the viewing space; wherein said cutting blade includes a distal end portion;

(d) means for extending the cutting blade outwardly from the viewing space in a manner such that said distal end portion of said cutting blade follows a path which is essentially perpendicular to the longitudinal axis of said probe;

(e) a grip handle rotatably connected to said probe; wherein said handle includes actuator means for extending said cutting blade;

(f) adjustment means for adjusting the rotational orientation between said lateral aperture of said probe and said grip handle; wherein said adjustment means is adapted to temporarily fix said rotational orientation; and (g) retraction means for automatically retracting said cutting blade upon release of said actuator means.

19. An instrument as recited in claim 18, wherein the probe is configured to be inserted into the carpal tunnel before the flexor retinaculum is divided.

20. An instrument as recited in claim 18, wherein the distal end is configured generally as an inclined plane which forms an acute angle with the upper surface of the probe.

21. An instrument as recited in claim 18, wherein the means for accepting an optical system accommodates a conventional examination telescope.

22. An instrument as recited in claim 18, wherein the means for extending the cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of the cutting blade; wherein said actuation shaft is adapted to respond to movement of said actuator means.

23. An instrument as recited in claim 22, wherein each additional increment of longitudinal displacement of the actuation shaft produces a correspondingly greater increment in the extension of the cutting blade.

24. An instrument as recited in claim 23, wherein the cutting blade is cooperatively engaged with pivot means in the distal end of the probe so that longitudinal displacement of the actuation shaft produces an angular displacement of the cutting blade as the actuation shaft approaches the pivot means, thereby outwardly extending the cutting blade.

25. An instrument in accordance with claim 22, wherein said cutting blade includes a proximal end which is pivotally connected to said actuation shaft; and further comprising elevating means for elevating said distal end portion of said cutting blade in response to longitudinal displacement of said actuation shaft.

26. An instrument in accordance with claim 22, wherein said probe is detachably connected to said grip handle; wherein said upper surface adjacent to said lateral aperture is flat; and wherein said actuation shaft is adapted to respond to actuating movement of a trigger carried by said grip handle.

27. An instrument in accordance with claim 18, further comprising marker means at said distal end of said probe for indicating the position of said distal end portion of said cutting blade relative to the longitudinal axis of said probe.

28. An instrument in accordance with claim 18, wherein said probe is detachably connected to said grip handle and is disposable.

29. An instrument in accordance with claim 18, wherein said probe includes a flat upper surface, parallel sides, and a convex lower surface.

30. A surgical instrument for manipulating selected tissue in a body cavity under visual inspection, comprising:

(a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface;

(b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;

(c) a working tool comprising blade means mounted within the probe and including a cutting blade capable of dividing selected tissue; wherein said cutting blade is capable of being extended from the viewing space; wherein said cutting blade includes a distal end portion;

(d) means for extending said cutting blade outwardly from the viewing space in a manner such that said distal end portion of said cutting blade follows a path which is essentially perpendicular to the longitudinal axis of said probe; wherein the means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of said cutting blade; wherein said actuation shaft is adapted to respond to actuating movement by an operator of the instrument; and wherein each additional increment of longitudinal displacement of the actuation shaft produces a correspondingly greater increment in the extension of said cutting blade.

(e) a grip handle rotatably connected to said probe; and (f) adjustment means for adjusting the rotation orientation between said lateral aperture of said probe and said grip handle; wherein said adjustment means is adapted to temporarily fix said rotational orientation.

31. An instrument in accordance with claim 30, further comprising marker means at said distal end of said probe for indicating the position of said distal end portion of said cutting blade relative to the longitudinal axis of said probe.

32. A surgical instrument for manipulating selected tissue in a body cavity under visual inspection, comprising:

(a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface;

(b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;

(c) a working tool comprising blade means mounted within the probe and including a cutting blade capable of dividing selected tissue; wherein said cutting blade is capable of being extended from the viewing space; wherein said cutting blade includes a distal end portion;

(d) means for extending said cutting blade outwardly from the viewing space in a manner such that said distal end portion of said cutting blade follows a path which is essentially perpendicular to the longitudinal axis of said probe; wherein said means for extending said cutting blade through the viewing space comprises (i) a longitudinally displaceable actuation shaft contained within the probe; wherein said cutting blade is pivotally connected to said actuation shaft, and (ii) a linking arm having first and second ends; wherein said first end is pivotally connected to said probe and said second end is pivotally connected to said cutting blade; wherein when said actuation shaft is moved toward said distal end of said probe said linking arm causes said distal end portion of said cutting blade to extend outwardly from said probe;

(e) a grip handle rotatably connected to said probe; and (f) adjustment means for adjusting the rotational orientation between said lateral aperture of said probe and said grip handle; wherein said adjustment means is adapted to temporarily fix said rotational orientation.

33. An instrument in accordance with claim 32, further comprising means for automatically retracting said cutting blade.

34. An instrument in accordance with claim 32, wherein said probe is detachably connected to said grip handle and is disposable.

35. An instrument in accordance with claim 32, further comprising marker means at said distal end of said probe for indicating the position of said distal end portion of said cutting blade relative to the longitudinal axis of said probe.

36. A surgical instrument for manipulating selected tissue in a body cavity under visual inspection, comprising:

(a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface;

(b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;

(c) a cutting blade mounted within the probe and capable of being extended from the viewing space; wherein said cutting blade includes a distal end portion and a proximal end; wherein said proximal end is pivotally connected to said probe;

(d) means for extending said cutting blade outwardly from the viewing space; wherein said means for extending said cutting blade comprises (i) a longitudinally displaceable actuation shaft contained within the probe; and (ii) a linking arm having first and second ends; wherein said first end is pivotally connected to said actuation shaft and said second end is pivotally connected to said cutting blade; wherein when said actuation shaft is moved toward said distal end of said probe said linking arm causes said distal end portion of said cutting blade to extend outwardly from said probe;

(e) a grip handle rotatably connected to said probe; and (f) adjustment means for adjusting the rotational orientation between said lateral aperture of said probe and said grip handle; wherein said adjustment means is adapted to temporarily fix said rotational orientation.

37. A disposable probe for use in a surgical instrument for manipulating selected tissue in a body cavity under visual observation, said probe comprising:

(a) an elongated tubular housing having proximal and distal ends; wherein said distal end is generally closed; wherein said housing includes an upper surface having a lateral aperture in said upper surface adjacent said closed distal end; wherein said distal end slopes away from said upper surface in a manner such that said distal end diverts displaceable tissue it contacts away from the region of said lateral aperture and said upper surface;

(b) an elongated cavity extending longitudinally through said housing for accepting an optical system;

(c) a working tool comprising blade means mounted within the housing adjacent said lateral aperture and including a cutting blade capable of dividing selected tissue; wherein said cutting blade includes a distal end portion;

(d) actuating means for extending said cutting blade outwardly from said probe in a manner such that said distal end portion of said cutting blade follows a path which is essentially perpendicular to the longitudinal axis of said housing.

38. A probe in accordance with claim 37, wherein said actuating means comprises an elongated actuation shaft having proximal and distal ends; wherein said cutting blade is pivotally connected to said distal end of said shaft; and further comprising elevating means for elevating said distal end portion of said cutting blade in response to longitudinal displacement of said shaft.

39. A surgical instrument for manipulating selected tissue in a body cavity under visual inspection, comprising:
  (a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface;
  (b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;
  (c) a working tool mounted within the probe and capable of being extended from the viewing space;
  (d) means for extending said tool outwardly from the viewing space; and
  (e) marker means at said distal end of said probe for indicating the position of said tool relative to the longitudinal axis of said probe.

40. An instrument in accordance with claim 39, wherein said working tool comprises blade means including a cutting blade having a distal end portion, wherein said marker means indicates the position of said distal end portion of said cutting blade.

41. An instrument in accordance with claim 39, further comprising:
  (f) a grip handle rotatably connected to said probe; and
  (g) adjustment means for adjusting the rotational orientation between said lateral aperture of said probe and said grip handle; wherein said adjustment means is adapted to temporarily fix said rotational orientation.

42. An instrument in accordance with claim 39, wherein said marker means comprises at least one vertical column adjacent said distal end of said probe.

43. An instrument in accordance with claim 42, wherein said marker means comprises two said vertical columns, wherein said vertical columns are spaced apart from each other within said viewing space.

44. A surgical instrument for manipulating selected tissue in a body cavity under visual inspection, comprising:
  (a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface;
  (b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;
  (c) a working tool comprising blade means mounted within the probe and including a cutting blade capable of dividing selected tissue; wherein said cutting blade is capable of being extended from the viewing space; wherein said cutting blade includes a distal end portion and a proximal end;
  (d) means for extending said cutting blade outwardly from the viewing space in a manner such that said distal end portion of said cutting blade follows a path which is essentially perpendicular to the longitudinal axis of said probe; wherein said means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of said cutting blade; wherein said proximal end of said cutting blade is pivotally connected to said actuation shaft; and further comprising elevating means for elevating said distal end portion of said cutting blade in response to longitudinal displacement of said actuation shaft; wherein said elevating means comprises:
    (1) a cam member carried by said cutting blade between said proximal end and said distal end portion; and
    (2) a cam track in said probe for receiving said cam member; wherein said cam track includes proximal and distal ends; and wherein said cam track is inclined upwardly from its said proximal end to its said distal end;
  wherein longitudinal displacement of said actuation shaft towards said distal end of said probe causes said cam member to move in said cam track along an inclined path, whereby said cutting blade pivots relative to said actuation shaft and extends outwardly from said probe;
  (e) a grip handle rotatably connected to said probe; and
  (f) adjustment means for adjusting the rotational orientation between said lateral aperture of said probe and said grip handle; wherein said adjustment means is adapted to temporarily fix said rotational orientation.

45. An instrument in accordance with claim 44, wherein said cam track includes upper and lower surfaces which are generally parallel to each other; wherein when said cutting blade is retracted from its extended position said cam member engages said upper surface of said cam track.

46. An instrument in accordance with claim 45, wherein said cam member comprises a guide pin projecting transversely outwardly from said cutting blade; wherein said lower surface of said cam track comprises an inclined ramp in said probe; and wherein said upper surface of said cam track comprises a clip member secured in said probe.

47. An instrument in accordance with claim 46, wherein said guide pin extends transversely through said cutting blade; and wherein there are two said cam tracks; and wherein said cam tracks are disposed adjacent opposite sides of said cutting blade.

48. An instrument in accordance with claim 44, wherein said probe includes a flat upper surface and parallel sides.

49. A surgical instrument for manipulating selected tissue in a body cavity under visual inspection, comprising:

(a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface; wherein said distal end further includes capture means;

(b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;

(c) a working tool comprising blade means mounted within the probe and including a cutting blade capable of dividing selected tissue; wherein said cutting blade is capable of being extended from the viewing space; wherein said cutting blade includes a distal end portion and a proximal end;

(d) means for extending said cutting blade outwardly from the viewing space in a manner such that said distal end portion of said cutting blade follows a path which is essentially perpendicular to the longitudinal axis of said probe; wherein said means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of said cutting blade; wherein said proximal end of said cutting blade is pivotally connected to said actuation shaft; and further comprising elevating means for elevating said distal end portion of said cutting blade in response to longitudinal displacement of said actuation shaft; and wherein said actuation shaft includes a distal end which is captured by said capture means when said cutting blade is in an outwardly extended position;

(e) a grip handle rotatably connected to said probe; and (f) adjustment means for adjusting the rotational orientation between said lateral aperture of said probe and said grip handle; wherein said adjustment means is adapted to temporarily fix said rotational orientation.

50. A surgical instrument for manipulating selected tissue in a body cavity under visual inspection, comprising:

(a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface;

(b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;

(c) a working tool comprising blade means mounted within the probe and including a cutting blade capable of dividing selected tissue; wherein said cutting blade is capable of being extended from the viewing space; wherein said cutting blade includes a distal end portion and a proximal end; wherein said cutting blade includes an elongated slot therein; wherein said cutting blade is cooperatively engaged with an axially fixed pivot in the distal end of the probe so that longitudinal displacement of the actuation shaft produces an angular displacement of said cutting blade as the actuation shaft approaches the pivot, thereby outwardly extending said cutting blade; wherein said pivot comprises a pin which extends through said slot;

(d) means for extending said cutting blade outwardly from the viewing space in a manner such that said distal end portion of said cutting blade follows a path which is essentially perpendicular to the longitudinal axis of said probe; wherein said means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of said cutting blade.

(e) a grip handle rotatably connected to said probe; and (f) adjustment means for adjusting the rotational orientation between said lateral aperture of said probe and said grip handle; wherein said adjustment means is adapted to temporarily fix said rotational orientation.

51. A surgical instrument for dividing the flexor retinaculum under visual inspection during carpal tunnel release, while minimizing the risk of injury to surrounding tissue, comprising:

(a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface; wherein said upper surface of said probe adjacent to said lateral aperture is configured generally as a flat or concave surface;

(b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;

(c) a cutting blade mounted within the viewing space and capable of being extended from the viewing space; wherein said cutting blade includes a distal end portion and a proximal end;

(d) means for extending the cutting blade outwardly from the viewing space in a manner such that said distal end portion of said cutting blade follows a path which is essentially perpendicular to the longitudinal axis of said probe; wherein said means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of the cutting blade; wherein said actuation shaft is adapted to respond to movement of said actuator means; wherein the means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of said cutting blade; wherein said proximal end of said cutting blade is pivotally connected to said actuation shaft; and further comprising elevating means for elevating said distal end portion of said cutting blade in response to longitudinal displacement of said actuation shaft; wherein said elevating means comprises:

(1) a cam member carried by said cutting blade between said proximal end and said distal end portion; and (2) a cam track in said probe for receiving said cam member; wherein said cam track includes proximal and distal ends; and wherein said cam track is inclined upwardly from its said proximal end to its said distal end;

wherein longitudinal displacement of said actuation shaft towards said distal end of said probe causes said cam member to move in said cam track along an inclined path, whereby said cutting blade pivots relative to said actuation shaft and extends outwardly from said probe;

(e) a grip handle rotatably connected to said probe; wherein said handle includes actuator means for extending said cutting blade;

(f) adjustment means for adjusting the rotational orientation between said lateral aperture of said probe and said grip handle; wherein said adjustment means is adapted to temporarily fix said rotational orientation; and (g) retraction means for automatically retracting said cutting blade upon release of said actuator means.

52. An instrument in accordance with claim 51, wherein said cam track includes upper and lower surfaces which are generally parallel to each other; wherein when said cutting blade is retracted from its extended position said cam member engages said upper surface of said cam track.

53. An instrument in accordance with claim 52, wherein said cam member comprises a guide pin projecting transversely outwardly from said cutting blade; wherein said lower surface of said cam track comprises an inclined ramp in said probe; and wherein said upper surface of said cam track comprises a clip member secured in said probe.

54. An instrument in accordance with claim 53, wherein said guide pin extends transversely through said cutting blade; and wherein there are two said cam tracks; and wherein said cam tracks are disposed adjacent opposite sides of said cutting blade.

55. A surgical instrument for dividing the flexor retinaculum under visual inspection during carpal tunnel release, while minimizing the risk injury to surrounding tissue, comprising:

(a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface; wherein said upper surface of said probe adjacent to said lateral aperture is configured generally as a flat or concave surface; wherein said distal end further includes capture means;

(b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;

(c) a cutting blade mounted within the viewing space and capable of being extended from the viewing space; wherein said cutting blade includes a distal end portion and a proximal end;

(d) an instrument as recited in claim 20, wherein the means for extending the cutting blade through the viewing space comprises a longitudinally displaceable actuation shaft contained with the probe, said actuation shaft being connected to said cutting blade in actuating relationship therewith providing means for transforming longitudinal displacement of the actuation shaft into outward extension of the cutting blade; wherein said actuation shaft is adapted to respond to movement of said actuator means; wherein said proximal end of said cutting blade is pivotally connected to said actuation shaft; and further comprising elevating means for elevating said distal end portion of said cutting blade in response to longitudinal displacement of said actuation shaft; and wherein said actuation shaft includes a distal end which is captured by said capture means when said cutting blade is in an outwardly extended position;

(e) a grip handle rotatably connected to said probe; wherein said handle includes actuator means for extending said cutting blade;

(f) adjustment means for adjusting the rotational orientation between said lateral aperture of said probe and said grip handle; wherein said adjustment means is adapted to temporarily fix said rotational orientation; and (g) retraction means for automatically retracting said cutting blade upon release of said actuator means.

56. A surgical instrument for manipulating selected tissue in a body cavity under visual inspection, comprising:

(a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface;

(b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;

(c) a working tool comprising blade means mounted within the probe and including a cutting blade capable of dividing selected tissue; wherein said cutting blade is capable of being extended from the viewing space; wherein said cutting blade includes a distal end portion and a proximal end;

(d) means for extending the cutting blade outwardly from the viewing space in a manner such that said distal end portion of said cutting blade follows a path which is essentially perpendicular to the longitudinal axis of said probe; wherein said means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of said cutting blade; wherein said actuation shaft is adapted to respond to actuating movement by an operator of the instrument; and wherein each additional increment of longitudinal displacement of the actuation shaft produces a correspondingly greater increment in the extension of said cutting blade; wherein the means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of said cutting blade; wherein said proximal end of said cutting blade is pivotally connected to said actuation shaft; and further comprising elevating means for elevating said distal end portion of said cutting blade in response to longitudinal displacement of said actuation shaft; wherein said elevating means comprises:

(1) a cam member carried by said cutting blade between said proximal end and said distal end portion; and (2) a cam track in said probe for receiving said cam member; wherein said cam track includes proximal and distal ends; and wherein said cam track is inclined upwardly from its said proximal end to its said distal end;

wherein longitudinal displacement of said actuation shaft towards said distal end of said probe causes said cam member to move in said cam track along an inclined path, whereby said cutting blade pivots relative to said actuation shaft and extends outwardly from said probe;

(e) a grip handle rotatably connected to said probe; and (f) adjustment means for adjusting the rotational orientation between said lateral aperture of said probe and said grip handle; wherein said adjustment means is adapted to temporarily fix said rotational orientation.

57. An instrument in accordance with claim 56, wherein said cam track includes upper and lower surfaces which are generally parallel to each other; wherein when said cutting blade is retracted from its extended position said cam member engages said upper surface of said cam track.

58. An instrument in accordance with claim 57, wherein said cam member comprises a guide pin projecting transversely outwardly from said cutting blade; wherein said lower surface of said cam track comprises an inclined ramp in said probe; and wherein said upper surface of said cam track comprises a clip member secured in said probe.

59. An instrument in accordance with claim 58, wherein said guide pin extends transversely through said cutting blade; and wherein there are two said cam tracks; and wherein said cam tracks are disposed adjacent opposite sides of said cutting blade.

60. A surgical instrument for manipulating selected tissue in a body cavity under visual inspection, comprising:

(a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface; wherein said distal end further includes capture means;

(b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;

(c) a working tool comprising blade means mounted within the probe and including a cutting blade capable of dividing selected tissue; wherein said cutting blade is capable of being extended from the viewing space; wherein said cutting blade includes a distal end portion;

(d) means for extending the cutting blade outwardly from the viewing space in a manner such that said distal end portion of said cutting blade follows a path which is essentially perpendicular to the longitudinal axis of said probe; wherein said means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of said cutting blade; wherein said actuation shaft is adapted to respond to actuating movement by an operator of the instrument; and wherein each additional increment of longitudinal displacement of the actuation shaft produces a correspondingly greater increment in the extension of said cutting blade; wherein said actuation shaft includes a distal end which is captured by said capture means when said cutting blade is in an outwardly extended position;

(e) a grip handle rotatably connected to said probe; and (f) adjustment means for adjusting the rotational orientation between said lateral aperture of said probe and said grip handle; wherein said adjustment means is adapted to temporarily fix said rotational orientation.

61. A disposable probe for use in a surgical instrument for manipulating selected tissue in a body cavity under visual observation, said probe comprising:
  (a) an elongated tubular housing having a proximal and distal ends; wherein said distal end is generally closed; wherein said housing includes an upper surface having a lateral aperture in said upper surface adjacent said closed distal end; wherein said distal end slopes away from said upper surface in a manner such that said distal end diverts displaceable tissue it contacts away from the region of said lateral aperture and said upper surface;
  (b) an elongated cavity extending longitudinally through said housing for accepting an optical system;
  (c) a working tool comprising blade means mounted within the housing adjacent said lateral aperture and including a cutting blade capable of dividing selected tissue; wherein said cutting blade includes a distal end portion;
  (d) actuating means for extending said cutting blade outwardly from said probe in a manner such that said distal end portion of said cutting blade follows a path which is essentially perpendicular to the longitudinal axis of said housing; wherein said actuating means comprises an elongated actuation shaft having a proximal and distal ends; wherein said cutting blade is pivotally connected to said distal end of said shaft; and
  (e) elevating means for elevating said distal end portion of said cutting blade in response to longitudinal displacement of said shaft; wherein said elevating means comprises:
    (1) a cam member carried by said cutting blade between said proximal end and said distal end portion; and
    (2) a cam track in said probe for receiving said cam member; wherein said cam track includes proximal and distal ends; and wherein said cam track is inclined upwardly from its said proximal end to its said distal end;
    wherein longitudinal displacement of said actuation shaft towards said distal end of said probe causes said cam member to move in said cam track along an inclined path, whereby said cutting blade pivots relative to said actuation shaft and extends outwardly from said probe;

62. A probe in accordance with claim 61, wherein said cam track includes upper and lower surfaces which are generally parallel to each other; wherein when said cutting blade is retracted from its extended position said cam member engages said upper surface of said cam track.

63. A surgical instrument for manipulating selected tissue in a body cavity under visual inspection, comprising:
  (a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface;
  (b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;
  (c) a working tool comprising blade means mounted within the probe and including a cutting blade capable of dividing selected tissue; wherein said cutting blade is capable of being extended from the viewing space; wherein said cutting blade includes a distal end portion and a proximal end;
  (d) means for extending the cutting blade outwardly from the viewing space in a manner such that said distal end portion of said cutting blade follows a path which is essentially perpendicular to the longitudinal axis of said probe; wherein said means for extending said cutting blade through the viewing space comprises a longitudinally displaceable actuation shaft contained within the probe, said actuation shaft being connected to said cutting blade in actuating relationship therewith providing means for transforming longitudinal displacement of the actuation shaft into outward extension of said cutting blade; wherein said proximal end of said cutting blade is pivotally connected to said actuation shaft; and further comprising elevating means for elevating said distal end portion of said cutting blade in response to longitudinal displacement of said actuation shaft; wherein said elevating means comprises:
    (1) a cam member carried by said cutting blade between said proximal end and said distal end portion; and
    (2) a cam track in said probe for receiving said cam member; wherein said cam track includes proximal and distal ends; and wherein said cam track is inclined upwardly from its said proximal end to its said distal end;
    wherein longitudinal displacement of said actuation shaft towards said distal end of said probe causes said cam member to move in said cam track along an inclined path, whereby said cutting blade pivots relative to said actuation shaft and extends outwardly from said probe;

* * * * *